United States Patent

Katocs, Jr. et al.

[11] Patent Number: 5,219,888
[45] Date of Patent: Jun. 15, 1993

[54] USE OF RETINOIDS FOR THE TREATMENT OF CORONARY ARTERY DISEASE

[75] Inventors: Andrew S. Katocs, Jr., Chestnut Ridge; Elwood Largis, Nanuet; Sotirios K. Karathanasis, Grandview, all of N.Y.

[73] Assignee: American Cyanamid Company, Wayne, N.J.

[21] Appl. No.: 860,814

[22] Filed: Mar. 31, 1992

[51] Int. Cl.[5] ............... A61K 31/20; A61K 31/07
[52] U.S. Cl. ............................ 514/560; 514/725; 514/824
[58] Field of Search ............... 514/560, 725, 824

[56] References Cited

PUBLICATIONS

Widom et al., Mol. Cell Biol., 12:3380–3389 (1992).
Widom et al., Mol. Cell Biol., 11:677–687 (1991).
Miller, N. E., Am. Heart J. 113:589–597 (1987).
Eisenberg, S., J. Lipid Res. 25:1017–1058 (1984).
Brattsand, Atherosclerosis, vol. 22, 1975, pp. 47–61.
Pawson et al., J. Med. Chem. 25: 1269–1277 (1982).
Rottman et al., Mol. Cell Biol., 11: 3814–3820 (1991).
Ringer et al., Am. J. Clin. Nutr., 53: 688–694 (1991).
Lyons et al., Br. J. Dermatology, 107: 591–595 (1982).

Primary Examiner—Frederick E. Waddell
Assistant Examiner—Kimberly R. Jordan
Attorney, Agent, or Firm—Kenneth J. Dow

[57] ABSTRACT

A method to increase plasma high density lipoprotein levels for the treatment and prevention of coronary artery disease by administering a therapeutic amount of a retinoid of the general formula:

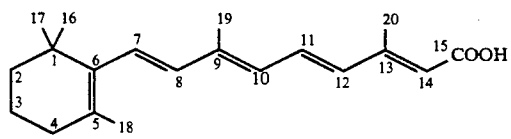

1 Claim, 1 Drawing Sheet

USE OF RETINOIDS FOR THE TREATMENT OF CORONARY ARTERY DISEASE

BACKGROUND OF THE INVENTION

1. Field of the Invention

The present invention relates to the therapeutic use of retinoids to increase plasma HDL levels for the treatment and prevention of coronary artery disease.

2. Description of the Related Art

High Density Lipoproteins (HDL), a heterogeneous population of spherical particles containing variable amounts of lipids and apolipoprotein, are the most abundant lipoproteins in the plasma. It has recently been observed that low plasma HDL levels are associated with an increased incidence of coronary artery disease (CAD). Numerous epidemiological studies over the last thirty years have verified this association and provided evidence for a putative protective effect of increased HDL levels against CAD; Miller, N. E., Am. Heart J. 113:589-597 (1987). It is believed that HDL plays a fundamental role in the lipid transport system and that HDL represents a site for transient storage of potentially harmful lipids and apolipoproteins which, if they were not packaged into lipoprotein particles, might damage cell membranes because of their potential detergent properties; Eisenberg, S., J. Lipid Res. 25:1017-1058 (1984).

It is known that high-density lipoproteins are involved in a large number of diverse intravascular metabolic processes including the process of reverse cholesterol transport, in which cholesterol from extrahepatic tissue is transported to the liver for conversion to bile acids and eventual excretion. As a result of these observations, research efforts have focused on methods of affecting plasma HDL levels in order to provide protection against CAD.

As stated above, HDL's are spherical particles containing variable amounts of lipoproteins and apolipoproteins. Apolipoprotein AI (Apo AI) is a major protein constituent of plasma HDL and intestinally derived lipoproteins known as chylomicrons. Although recent studies suggest that dietary, hormonal and other environmental factors regulate apo AI gene expression, the molecular basis for the mechanisms involved remain poorly understood. It is known that the gene coding for apolipoprotein AI is expressed predominantly in the liver and intestine. Previous work has shown that hepatocyte-specific expression is determined by synergistic interactions between transcription factors bound to three separate sites with a powerful liver-specific enhancer located in the region $-222$ to $-110$ nucleotides upstream of the apolipoprotein AI start site; Widom et al., Mol. Cell Biol., 11:677-687 (1991). In a recent study, it was found that one of the sites in this enhancer is a highly specific retinoic acid-responsive element (RARE) that responds to recently identified retinoic acid receptors (RXR$\alpha$); Rottman et al., Mol. Cell Biol., 11:3814-3820 (Jul. 1991). These results suggest that retinoic aid response pathways mediated by RXR$\alpha$ play a role in apolipoprotein AI expression and ultimately cholesterol and retinoid transport and metabolism.

It has been known for many years that retinoids, the family of molecules comprising both the natural and synthetic analogues of retinol (Vitamin A), are potent agents for control of both cellular differentiation and cellular proliferation; Wolbach et. al., J. Exp. Med., 42:753-777. Retinoids have been reported to modulate the growth and progression of tumors and premalignant lesions, to affect the immune system, to play a role in inflammatory processes, to regulate differentiation of tissues (especially epithelial) and organs and to influence cellular adhesiveness and cellular interactions. See Pawson et al., J. Med. Chem., 25:1269-1277 (1982).

Ringer et al., Am. J. Chem Nutr., 53:688-694 (1991) observed an increase in HDL concentrations in patients given $\beta$-carotene, but did not find any changes in apolipoprotein A or B levels. Gollnick et al., Saurat (ed.), Retinoids: New Finds in Research and Therapy, Retinoid Symp., Geneva 1984, pp. 445-460 (Karger, Basel 1985), reported no significant alteration in the HDL and LDL fractions of cholesterol in patients given etretinoate, and a decrease in HDL-cholesterol under isotretinoin. Lyons et al., Br. J. Dermatology, 107:591-595 (1982) observed a decrease in HDL-cholesterol levels in patients given 13-cis-retinoic acid.

SUMMARY OF THE INVENTION

The present invention relates to the therapeutic use of retinoids to increase plasma HDL levels for the treatment and prevention of coronary artery disease and to protect against premature atherosclerosis. Suitable therapeutic agents for the practice of this invention include various retinoids. As conventionally defined, retinoids are a class of compounds consisting of four isoprenoid units joined in a head-to-tail manner. All retinoids may be formally derived from a monocyclic parent compound containing five carbon-carbon double bonds and a functional group at the terminus of the acyclic portion. Representative of these compounds is retinoic acid having the formula:

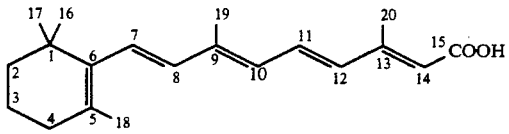

Although retinoic acid, more particularly, trans-retinoic acid and retinol, more particularly, all trans-retinol, are preferred, it is also believed that other retinoid compounds may be successfully used in the practice of this invention to increase plasma HDL levels. Such compounds include all trans-retinoic acid (tretinoin), retinoic acid methyl ester, retinoic acid ethyl ester, phenyl analog of retinoic acid, retinyl acetate, retinaldehyde and 9-cis retinoic acid. These compounds, their chemistry and synthesis, are described in Frickel, F., Chemistry and Physical Properties of Retinoids: THE RETINOIDS, Sporn, Roberts, Goodman, Eds., Academic Press, p. 7-145 (1984).

DETAILED DESCRIPTION

Figure 1:
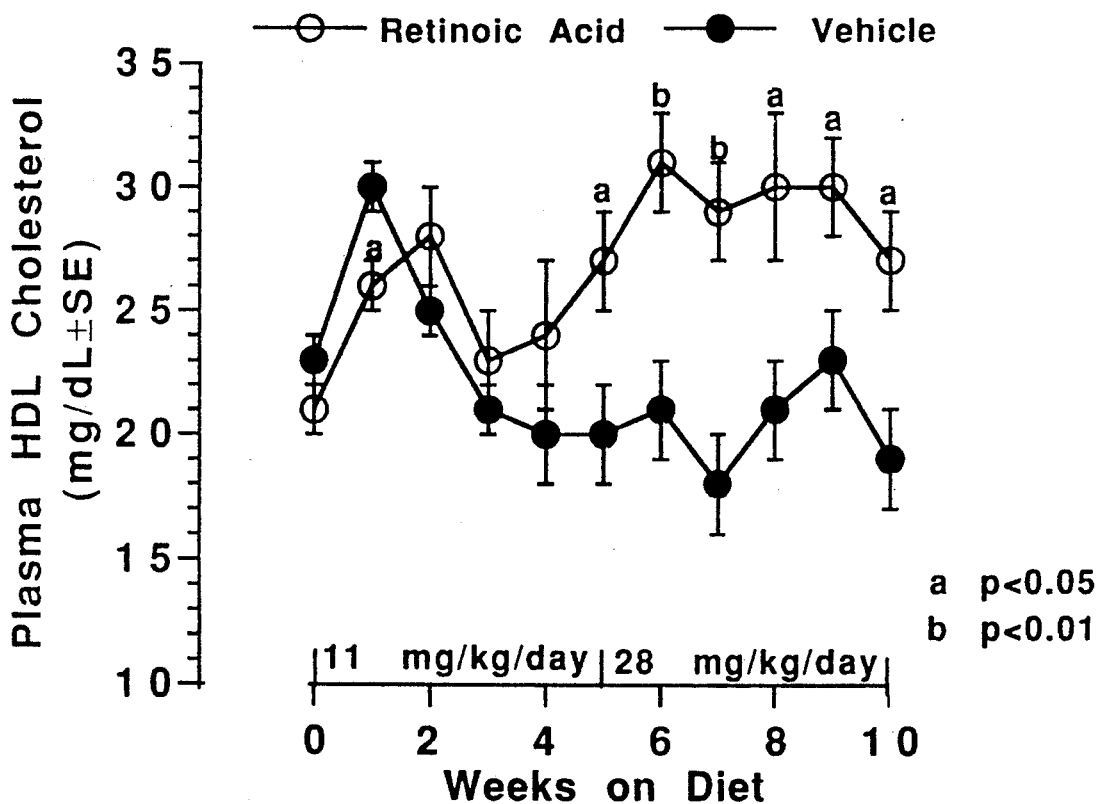
FIG. 1 is a graph showing the effect of retinoic acid on plasma HDL cholesterol in peanut oil fed rabbits.

As stated above, apoAI is the major protein constituent of plasma HDL. Numerous epidemiologic, genetic and biochemical studies have provided strong support for the concept that high plasma HDL concentrations protect against premature atherosclerosis. Indeed, it has been previously shown that disruption of the apoAI and nearby apoCIII genes due to a DNA inversion in the genome of certain patients with premature coronary heart disease causes combined apoAl, apoCIII and HDL plasma deficiency and accelerated atherosclerosis; Karathanasis et al., Apolipoprotein Mutants 2, Sirtori et al., (eds.) p. 143-155 (1989). Thus, the observation that there is a direct correlation between apoAI and HDL plasma levels and hepatic apoAI mRNA concentrations (Sorci-Thomas et al., *J. Biol Chem.* 263:5183-5189 (1988)) and the results of a recent study showing that retinoic acid transactivates apoAI gene expression raises the possibility that retinoic acid and other Vitamin A metabolites may play an important role in atherosclerosis prevention. In this context, studies were conducted to determine whether retinoic acid has an effect on plasma HDL levels.

PROTOCOL FOR TEN WEEK ALL TRANS RETINOIC ACID STUDY

Male New Zealand rabbits weighing between 2.0-2.7 kg were placed on rabbit pellets supplemented with 6% peanut oil with and without all trans retinoic acid. The rabbits were fed 125 g of diet daily during the dark cycle such that the average dose of retinoic acid was 11 mg/kg/day for the first 5 weeks of the experiment and 28 mg/kg/day for the next 5 weeks. For the low and high dose of all trans retinoic acid, 2 and 6 g, respectively, were suspended in 600 ml of peanut oil and hand mixed into 10 kg of rabbit pellets. Approximately 10 ml of arterial blood was collected from the major artery of the ear from each rabbit on a weekly basis. The samples were centrifuged at 3000 rpm at 4° C. for 15 minutes. The resultant plasma samples were frozen at $-70°$ C. Upon thawing the samples were analyzed for HDL cholesterol levels and submitted for clinical chemistry determinations. Body weights were monitored on a weekly basis and food consumption on a daily basis. At the end of the study, the rabbits were sacrificed by pentobarbital sodium overdose via the marginal ear vein. Samples of the liver and small intestine were removed and placed in liquid nitrogen and then into a $-70°$ C. freezer. These tissues will be analyzed for the expression of apolipoprotein Al mRNA. The results of this study are set forth in Table I and FIG. I.

to that described above in the ten week protocol. The results are set forth in Table II.

TABLE II

Effect of All Trans Retinoic Acid on Plasma HDL Cholesterol Levels in Rabbits Supplemented With Peanut Oil
HDL Cholesterol (mg/dL ± SE)

| Dose mg/kg/day | Week | | | | |
|---|---|---|---|---|---|
| | 0 | 1 | 2 | 3 | 4 |
| 0a | 26 ± 2 | 28 ± 2 | 25 ± 3 | 25 ± 2 | 21 ± 3 |
| 11$^a$ | 25 ± 3 | 33 ± 3 | 32 ± 3 | 31 ± 2 | 30 ± 3$^c$ |
| 23$^a$ | 25 ± 3 | 30 ± 3 | 31 ± 2 | 31 ± 2 | 30 ± 2$^d$ |
| 32$^b$ | 26 ± 4 | 33 ± 5 | 36 ± 6 | 35 ± 5 | 30 ± 5 |
| 40$^a$ | 25 ± 3 | 34 ± 4 | 36 ± 3$^c$ | 35 ± 3$^c$ | 32 ± 4$^c$ |

$^a$n = 8
$^b$n = 6
$^c$p<0.05
$^d$p<0.01

The foregoing results show that during the first 5 weeks of the study, plasma HDL cholesterol levels increased transiently in both the control and drug treated groups and then fell back to pre-dose levels by the third week. During the last 5 weeks of the study, retinoic acid at an average dose of 28 mg/kg/day but not peanut oil produced a 50% increase in plasma HDL cholesterol levels. During this time period HDL protein was increased by 15% and phospholipids by 50% in the retinoic acid treated animals. There were no significant increases in plasma triglycerides or LDL-VLDL cholesterol in either control or retinoic acid treated animals. Retinoic acid was well-tolerated with no effect on food consumption although body weight gain was decreased during the last five weeks of the study. The only anomaly in plasma chemistry was an elevation of alkaline phosphatase levels in retinoic acid treated animals at both doses. Whether the mechanism for the observed increase in plasma HDL cholesterol levels is due to increased transcriptional rates of the apoAl gene in the retinoic acid treated animals is currently under investigation.

In accordance with the present invention, the retinoids may be administered orally in association with a pharmaceutically acceptable carrier to humans for the

TABLE I

Effect of All Trans Retinoic Acid on Plasma Cholesterol Levels in Rabbits Supplemented With Peanut Oil
HDL Chloesterol (mg/dL ± SE)

| Treatment | Week | | | | | | | | | | |
|---|---|---|---|---|---|---|---|---|---|---|---|
| | 0 | 1 | 2 | 3 | 4 | 5 | 6 | 7 | 8 | 9 | 10 |
| Control | 23 ± 1 | 30 ± 1 | 25 ± 1 | 21 ± 1 | 20 ± 2 | 20 ± 2 | 21 ± 2 | 18 ± 2 | 21 ± 2 | 23 ± 2 | 19 ± 2 |
| Retinoic Acid$^a$ | 21 ± 1 | 26 ± 1$^b$ | 28 ± 2 | 23 ± 2 | 24 ± 3 | 27 ± 2$^b$ | 31 ± 2$^c$ | 29 ± 2$^c$ | 30 ± 3$^b$ | 30 ± 2$^b$ | 27 ± 2$^b$ |

$^a$11 mg/kg/day for the first 5 weeks and 28 mg/kg/day for the last 5 weeks
$^b$p<0.05
$^c$p<0.01

PROTOCOL FOR THE DOSE RESPONSE STUDY

Male New Zealand rabbits weighing between 2.3-2.9 kg were grouped according to plasma HDL cholesterol and placed on rabbit pellets supplemented with 6% peanut oil with and without all trans retinoic acid for four weeks at four doses. The rabbits were fed 125 g of diet daily during the dark cycle such that the average doses of all trans retinoic acid were 11, 23, 32 and 40 mg/kg/day. For these doses of all trans retinoic acid, 2.3, 4.6, 6.9 and 9.2 g, respectively, were suspended in 600 ml of peanut oil and hand mixed into 10 kg of rabbit pellets. The animals were handled in a manner identical treatment or prevention of coronary artery disease or atherosclerosis.

When the compounds are employed for the above utility, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds may also be encapsulated in liposomes to allow an intravenous administration of the drug. The liposomes suitable for use in this invention are lipid vesicles and may include plurilamellar lipid vesicles, small sonicated multilamellar vesicles, reverse phase evaporation vesicles, large multilamellar vesicles and the like wherein the lipid vesicles are formed of one or more phospholipids such as phosphotidylcholine, phosphatidylglycerol, sphingomyelin, phospholactic acid and the like. In addition, the liposomes may also comprise a sterol component such as cholesterol.

We claim:

1. A method of increasing plasma HDL levels in a mammal which comprises administering a pharmacologic amount effective to increase said plasma HDL levels of a compound selected from the group consisting of the retinoids all trans-retinoic acid, and 9-cis-retinoic acid.

* * * * *

Adverse Decision In Interference

Patent No. 5,219,888, Andrew S. Katocs, Elwood Largis, Sotirios K. Karathanasis, USE OF RETINOIDS FOR THE TREATMENT OF CORONARY ARTERY DISEASE, Interference No. 103,931, final judgment adverse to the patentees rendered September 20, 2002, as to claim 1.

*(Official Gazette November 26, 2002)*